(12) United States Patent
Gabrio et al.

(10) Patent No.: US 6,615,826 B1
(45) Date of Patent: Sep. 9, 2003

(54) SLOW SPRAY METERED DOSE INHALER

(75) Inventors: Brian J. Gabrio, Oakdale, MN (US); David J. Velasquez, Cannon Falls, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 09/510,388

(22) Filed: Feb. 22, 2000

Related U.S. Application Data

(60) Provisional application No. 60/121,878, filed on Feb. 26, 1999.

(51) Int. Cl.[7] .............................................. A61M 11/00
(52) U.S. Cl. .......................... 128/200.23; 128/200.14; 128/203.12
(58) Field of Search ...................... 128/200.14–200.23, 128/203.23, 207.14

(56) References Cited

U.S. PATENT DOCUMENTS

| | | | |
|---|---|---|---|
| 4,926,852 A | | 5/1990 | Zoltan et al. |
| 4,972,830 A | | 11/1990 | Wong et al. |
| 5,571,246 A | * | 11/1996 | Alldredge ............... 128/200.23 |
| 5,758,638 A | | 6/1998 | Kreamer |
| 5,899,201 A | * | 5/1999 | Schultz et al. ......... 128/200.23 |
| 6,062,214 A | * | 5/2000 | Howlett .................. 128/200.23 |

FOREIGN PATENT DOCUMENTS

| | | |
|---|---|---|
| DE | 1219090 | 1/1971 |
| EP | 412648 B1 | 2/1991 |
| FR | 2511250 | 2/1983 |
| GB | 2104393 | 3/1983 |
| GB | 2279879 | 1/1995 |
| WO | 93/05837 | 3/1993 |
| WO | 93/09830 | 5/1993 |

OTHER PUBLICATIONS

S.P. Newman, A.R. Clark, N. Talee & S.W. Clarke, "Pressurised aerosol deposition in the human lung with and without an "open" spacer device", Thorax, vol. 44, pp. 706–710 (1989).

S. P. Newman & S.W. Clarke, "Bronchodilator Delivery From Gentlehaler, A New Low–Velocity Pressurized Aerosol Inhaler", Chest, vol. 103, No. 5, pp. 1442–1446 (May, 1993).

D.J. Velasquez and B. Gabrio, Metered Dose Inhaler Aerosol Deposition in a Model of the Human Respiratory System and a Comparison with Clinical Deposition Studies, Journal of Aerosol Medicine, 11 (Suppl. 1) : S23–S28, (1998).

* cited by examiner

Primary Examiner—Glenn K. Dawson
(74) Attorney, Agent, or Firm—Ted Ringsred

(57) ABSTRACT

A pressurized metered dose inhaler having an actuator constructed and arranged so as to inhibit airflow due to patient inhalation in the vicinity of the orifice of the nozzle block when the valve stem is in its dispensing position. This design reduces unwanted oropharyngeal deposition of medicament and increases the relative amount of medicament to the lung.

5 Claims, 5 Drawing Sheets

SLOW SPRAY METERED DOSE INHALER

This is a continuation-in-part of provisional Application No. 60/121,878 filed Feb. 26, 1999.

FIELD OF THE INVENTION

This invention relates to an inhaler for medicament and in particular to an inhaler for transferring to the respiratory system of a patient a metered dose of medicament contained in a pressurised dispensing canister.

BACKGROUND OF THE INVENTION

In known metered dose inhalers, the aerosol stream comprising liquefied propellant and medicament from a pressurised dispensing canister is fired into a chamber towards a mouthpiece of the inhaler into an air space that allows airflow travelling in the same direction via openings to the outside air. In known devices at actuation, a user inhales through a mouthpiece of the inhaler and creates an airflow through the chamber from air inlets which are generally at a part of the inhaler located upstream from the mouthpiece. Upon actuation, the medicament is then released into this airflow at a point between the air inlets and the mouthpiece so that it is travelling in the same direction as the airflow. Typically in such devices, there is little restriction in the airflow between the air inlets and the mouthpiece. Because of this, a substantial airflow may be created by a user of the device and, because the medicament is fired into the airflow in the same direction as the airflow, the effect is that particles of medicament can be travelling at quite substantial velocities e.g. in excess of 40 m/s when they reach the mouthpiece. As inhalers of this type are normally designed to be as small as practical for the convenience of users, the distance between the point at which the medicament is fired into the airflow and the patient's mouth is usually quite small so that there is little distance to reduce the inertia of the particles of medicament with the result that the particles may impact and deposit in the oropharynx rather than being carried with inhaled air into the lungs. This is normally quite undesirable, since the medicaments were designed for delivery to the respiratory system and may not have an appropriate effect when deposited in the oropharynx and allowed to enter the digestive tract.

In an effort to overcome this problem, devices have been produced in which the medicament is fired into a holding volume, commonly called a Spacer, which allows the velocity of the medicament to be reduced and also allows some propellant evaporation to occur. Spacers can improve the performance of a metered dose inhaler by reducing oropharyngeal deposition, see S. P. Newman & S. W. Clarke, Chest, vol 103 (5) pp. 1442–1446 (1993) Bronchodilator Delivery From Gentlehaler, A New Low-Velocity Pressurized Aerosol Inhaler and S. P. Newman, A. R. Clark, N. Talee & S. W. Clarke, Thorax, vol 44 pp.706–710 (1989), Pressurised aerosol deposition in the human lung with and without an "open" spacer device.

However, these devices with a holding volume and other spacer devices tend to be of significantly larger size than the conventional metered dose inhalers and therefore less convenient and attractive to users.

Various attempts have been made to modify the spray characteristics of inhalers.

GB-A-2279879 discloses an inhaler in which the air inlets are arranged such that during inhalation an airflow is created which has a component directed away from the mouthpiece towards the aerosol spray. The reverse airflow component is intended to create turbulence and slow the velocity of the medicament particles.

WO93/05837 and U.S. Pat. No. 4,972,830 disclose inhalers in which the passage which directs the pressurised medicament from the canister to the chamber has particular configurations to reduce the velocity of the spray and enhance dispersion of the medicament in the airflow.

EP-A-0412648 discloses an inhaler in which a frusto-conical diverter with a small orifice is positioned in the path of the spray before the mouthpiece. Aerosol droplets are said to predominantly pass through the small orifice, decelerate and be inhaled while the propellant gas is predominantly diverted away from the mouthpiece out of the inhaler.

It is known to modify the airflow through an inhaler to achieve particular effects. WO93/09830 discloses an inhaler which is constructed and arranged to prevent inhalation through the device prior to the dose being fired. The object of the arrangement is to synchronise inhalation and firing the dose to ensure the dose is dispensed during inhalation. U.S. Pat. No. 5,758,638 discloses an inhaler which includes an air port so that during inhalation flow of air through the port activates an audio or visual signal generates, such as a whistle or flag, that signals to the user that the user is inhaling and that the conditions are appropriate for the administration of the medicament.

Similarly for intranasal inhalers it is desirable to reduce the velocity of the spray in the interests of patient comfort and efficacity.

SUMMARY OF THE INVENTION

The present invention provides alternative constructions of an inhaler which reduce the velocity of the spray exiting the mouthpiece or nasal adapter.

According to the present invention there is provided an inhaler for medicament comprising an aerosol canister containing a pressurised medicament formulation equipped with a metered dose dispensing valve having a valve stem movable between non-dispensing and dispensing positions, and an actuator comprising a housing adapted to receive the aerosol container and defining a chamber having one or more air inlets and a patient port in the form of a mouthpiece or nasal adapter, and a nozzle block adapted to receive the valve stem of the dispensing valve, the nozzle block comprising a passage in communication with the valve stem and terminating in an orifice for directing medicament from the valve stem into the chamber, in which the actuator is constructed and arranged to inhibit patient-induced airflow in the vicinity of the orifice of the nozzle block when the valve stem is in its dispensing position.

The inhaler of the invention may be constructed such that airflow due to patient inhalation is prevented or reduced in the vicinity of the orifice at all times or only during dispensing of the medicament from the valve. Either arrangement has the effect of substantially reducing the velocity of the emitted spray compared to an inhaler which allows free flow of air in the vicinity of the nozzle block during dispensing of the medicament. It is possible to modify existing press and breathe inhalers to prevent such airflow by the provision of a suitable gasket.

It has been discovered that the velocity of an aerosol spray from a metered dose inhaler is significantly influenced by the presence of an open conduit in the vicinity of the nozzle through which the spray emerges. The spray exits the nozzle as a high velocity stream which creates low pressure regions. The ability of the free-flowing air entering through air vents to fill the low pressure regions influences the velocity of the emitted spray. If a free flow of air is allowed in the vicinity of the nozzle, as in a standard press-and-breathe inhaler where the patient breathes through the mouthpiece and an airflow is established around the canister and nozzle to the mouthpiece, the emitted spray maintains a high velocity. If the actuator is sealed to outside airflow in the vicinity of the nozzle, the low pressure regions cannot immediately be occupied by the surrounding air and the low pressure regions exert a retarding influence on the stream emanating from the nozzle, thereby causing the stream to lose velocity.

It has been found that inhibiting make-up, or free-flowing air in the vicinity of the nozzle when the spray is generated significantly reduces the velocity of the emitted spray and spray force from the mouthpiece, resulting in an extremely soft, low velocity spray plume.

The vicinity of the orifice includes on all sides upstream to the temporary or permanent closure behind the nozzle block, and downstream to the first communication with the outside atmosphere. That is, during dispensing there is no communication to the outside atmosphere for the region surrounding the orifice of the nozzle block. There is no communication with the outside atmosphere via the air inlets upstream to the orifice of the nozzle block and no communication with the outside atmosphere downstream of the orifice of the nozzle block for a distance sufficient to allow the aerosol stream to develop sufficient turbulence to stop its downstream momentum. For example, the stream exiting 0.30 mm to 0.50 mm orifice would not be in communication with the outside atmosphere via the upstream air inlets and the stream would be in communication with outside air being drawn into the device at a downstream distance relative to the orifice of 4 to 6 cm. The location downstream of the orifice at which the outside air is drawn into the device may vary from 0 to 15 cm depending on the orifice diameter and mouthpiece diameter.

Radioscintigraph tests have revealed that when airflow is prevented or restricted in the vicinity of the nozzle the flow of the spray becomes turbulent within the chamber. The turbulent zone is generally formed between about 3 to 5 cm from the nozzle for a nozzle orifice of approximately 0.30 mm. The high degree of turbulence causes a large reduction in the linear velocity of the spray as well as an increase in the deposition of drug particles on the wall of the chamber. If the chamber and mouthpiece are of sufficient length to encompass this turbulent zone the result is a significant reduction in the kinetic energy of the stream delivered to the patient. Preferably, the actuator is constructed such that the distance from the nozzle to the mouthpiece is from approximately 1 to 15 cm, preferably 4 to 6 cm, with a chamber/mouthpiece diameter from 1 to 4 cm, 0.5 to 1 cm in the case of a nasal adapter.

The actuator must possess air inlets which enable the patient to inhale though the patient port without encountering significant resistance since the patient may have breathing difficulties when taking the medication e.g. during an asthma attack. However, the air inlets, for example in the mouthpiece, must not concentrate the airflow into too narrow an area, as this will give a high velocity of incoming air which will deflect the spray onto the wall of the mouthpiece opposite the air inlets.

In one embodiment of the invention the air inlets are positioned downstream of the nozzle, in the region of the turbulent zone and/or downstream of the turbulent zone. The positioning and direction of the air inlets may also affect the deposition of medicament within the chamber and mouthpiece. In one arrangement air inlets comprise a series of holes, within or downstream of the turbulent zone adjacent the mouthpiece directing air perpendicular to the aerosol stream. In a second arrangement the air inlets are directed towards the outlet of the mouthpiece to introduce a sheath of air around the aerosol stream, parallel to the aerosol stream. In a third arrangement the air inlets are arranged, optionally interdispersed with baffles on the wall of the chamber, to direct air into the turbulent zone to mix air with the aerosol stream. In a fourth arrangement the air inlets are positioned at the downstream end or downstream of the turbulent zone and direct air back towards the turbulent zone. In a further arrangement a mouthpiece is constructed of porous material to allow a multiplicity of finely divided air vents to provide air flow over a larger surface area. The diffuse airflow through the mouthpiece also tends to keep the formulation stream away from the mouthpiece wall, thereby reducing drug deposition on the walls.

In a second embodiment of the invention the actuator may possess air inlets upstream of or in the vicinity of the nozzle but the air inlets are blocked when the valve is fired to release the aerosol spray. The air inlets are opened after the spray has been released by which time the velocity of the stream will have been reduced and the turbulent zone formed. Upon inhalation an airflow will be established from the air inlets to the mouthpiece which entrains the residual aerosol spray. The actuator may include additional air inlets downstream of the nozzle, as described above with respect to the first embodiment. These downstream air inlets do not need to close during release of the aerosol spray.

A third embodiment uses a porous membrane to introduce air into or downstream of the turbulent zone. The advantage of the membrane is that the air is introduced more uniformly and diffusely around the circumference of the spray, thereby acting as a buffer between the turbulent flow and the wall. The effect is to reduce drug deposition in the device. The membrane may optionally be protected from dirt or contact by the users lips by an additional part of the mouthpiece. This embodiment may be used in combination with embodiment 1 or 2. Additionally, this embodiment may be incorporated without the restricting or preventing of airflow in the vicinity of the nozzle.

For certain medicaments it is particularly desirable to reduce contact between the medicament and parts of the body it is not intended for. For example, residues of the medicament deposited on internal surfaces of actuators may be fingered and transferred to other body parts. A fourth embodiment of the invention incorporates a baffle to allow the spray to pass through, whilst limiting access by the patient to internal surfaces of the actuator.

A fifth embodiment of the invention is configured for intranasal delivery.

It is known that the size of the orifice in the nozzle may affect the spray characteristics. Smaller orifices tend to produce aerosols of small droplet size which lead to improved respirable fraction. However, smaller orifices are more difficult to manufacture. The actuator of the invention significantly reduces the spray velocity regardless of the orifice size. It has been shown to reduce oropharyngeal deposition with orifices in the size range 0.010 to 0.025 inch and the deposition for these two sizes was found not to differ significantly.

BRIEF DESCRIPTION OF THE DRAWINGS

The invention will now be described with reference to the accompanying drawings in which.

DETAILED DESCRIPTION

Figure 1:
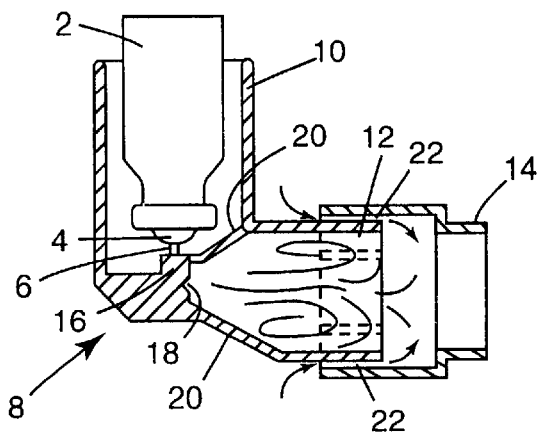
FIG. 1 represents a cross-section through an inhaler in accordance with one embodiment of the invention.

The inhaler of FIG. 1 comprises an aerosol canister (2) equipped with a metered dose dispensing valve (4) having a valve stem (6). The actuator, generally shown at (8), comprises a housing (10) which receives the aerosol container (2), a chamber (12) and a mouthpiece (14). A nozzle block (16) receives the valve stem (6) and has a passage (not shown) terminating in an orifice (18) which directs spray from the aerosol valve into the chamber. The housing comprises solid walls (20) in the vicinity of the nozzle block so that there can be no air flow through the device in the vicinity of the orifice. Air inlet passages (22) are positioned towards the end of the chamber (12) and are directed towards the mouthpiece (14).

When the aerosol valve is fired, a metered dose of aerosol formulation exits the orifice (18) in to chamber (14). There is no air flow in the vicinity of the orifice (18). Consequently the spray is rapidly decelerated and a turbulent zone is formed shown generally by the curved lines within the chamber (12). As the patient breathes through the mouthpiece (14) air passes through the inlets (22) towards the mouthpiece (14) forming a sheath of air around the spray of aerosol formulation. The inhaler provides substantially reduced deposition in the oropharynx of the patient compared with a standard press-and-breathe inhaler without compromising the respirable fraction unduly.

Figure 2:
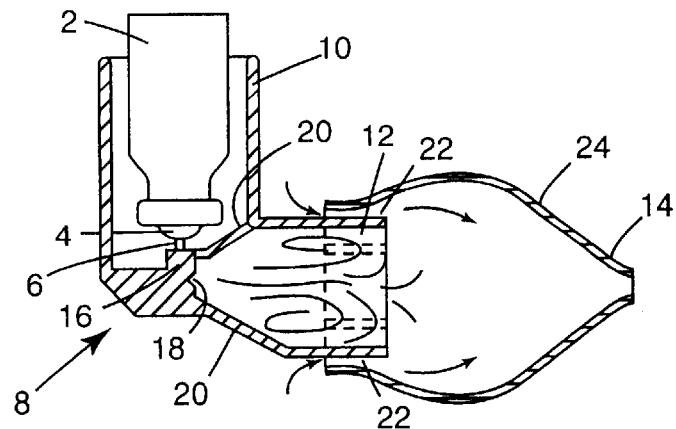
FIG. 2 represents a cross-section through an inhaler according to a second embodiment of the invention.

FIG. 2 of the accompanying drawings illustrates a second embodiment of the invention which is similar to FIG. 1 and like numerals represent like parts. The difference in the embodiment shown in FIG. 2 is that the mouthpiece (14) has a bulbed configuration (24) to provide an increase in cross-sectional area of the mouthpiece downstream of the turbulent zone followed by a decrease in cross-sectional area at the extreme downstream end of the mouthpiece. The arrangement of air inlets is similar to that shown in FIG. 1, the bulbed configuration acts in a similar manner to a conventional spacer.

Figure 3:
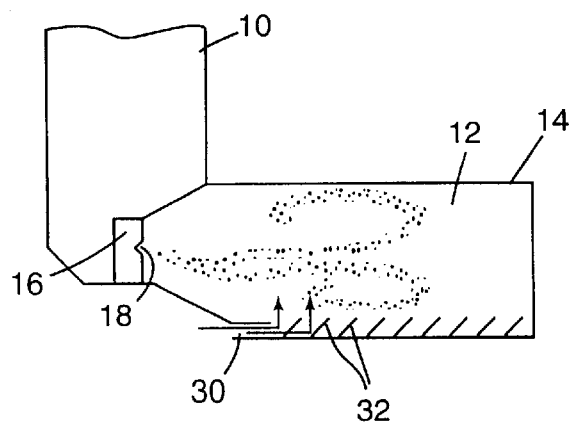
FIG. 3 represents a diagrammatic cross-section of a portion of an inhaler in accordance with a further embodiment of the invention.

FIG. 3 is a diagrammatic cross-section through a portion of an inhaler having an alternative construction of air inlets. In this embodiment the air inlets (30) are arranged downstream of the nozzle block and have associated baffles (32) such that incoming air is deflected in to the turbulent zone of the aerosol spray shown by the curved lines within the chamber (12). The air inlets and baffles can extend throughout the circumference of the chamber or may be located towards the bottom of the chamber. The baffles may continue throughout the length of the chamber to the mouthpiece to facilitate turbulence of the airflow.

Figure 4:
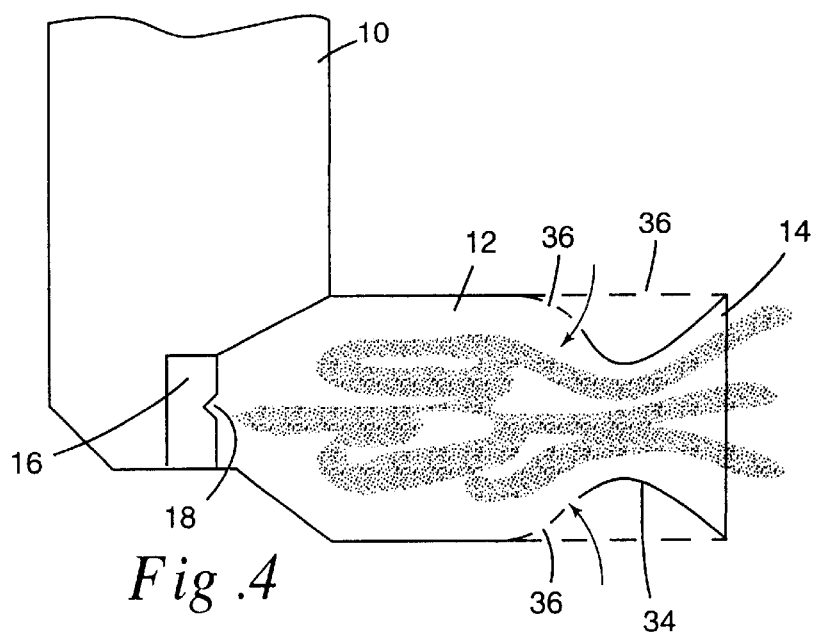
FIG. 4 represents a partial diagrammatic cross-section of a further inhaler in accordance with the invention.

FIG. 4 of the accompanying drawings is a diagrammatic cross-section of a portion of an inhaler in accordance with the invention. The downstream end of the chamber is shaped to form a venturi (34) and the air inlet ports (36) are arranged such that air enters in a direction towards the turbulent zone. The aerosol spray is expanded through the venturi as it reaches the mouthpiece (14).

Figure 5A:
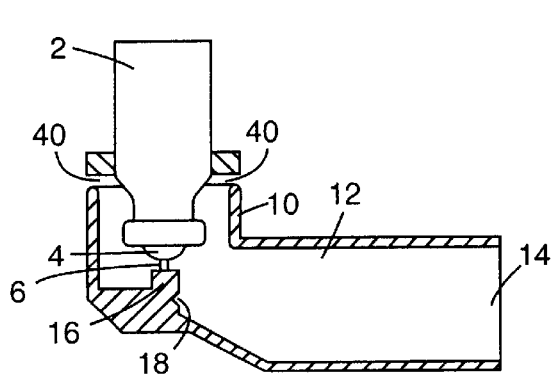
FIGS. 5a, 5b and 5c represent a cross-section of a further inhaler in accordance with the invention.
Figure 5B:
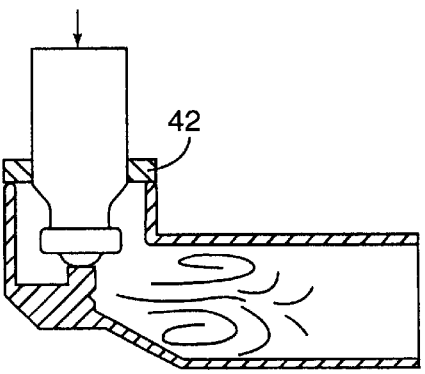
Figure 5C:
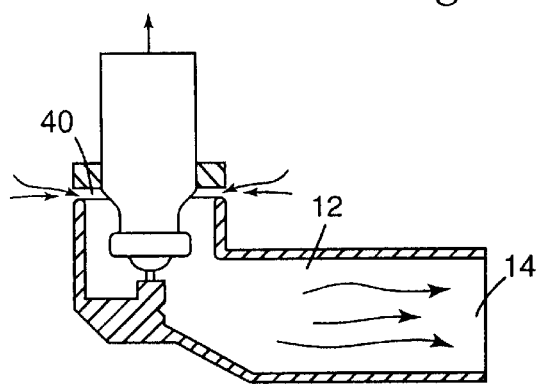

FIGS. 5a to 5c represent a cross-section through an alternative inhaler in accordance with the invention. In this embodiment, when the valve (4) is in its non-dispensing position air inlet ports (40) formed between the canister (2) and the housing (10) are open (FIG. 5a). When the valve (4) is in its dispensing position caused by moving the canister (2) relative to the valve stem (6) (FIG. 5b), seal 42 around the canister (2) closes the air inlet ports (40). Thus, during firing of the aerosol spray, there is no airflow in the vicinity of the orifice (18) and the spray will decelerate and form a turbulent zone within the chamber (12) shown by the curved lines. Thereafter, the patient releases the canister (2) which returns the valve to the non-dispensing position (FIG. 5c) and during inhalation at the mouthpiece (14) an airflow is established through the air inlets (40) to the mouthpiece (14) via the chamber (12) thereby entraining the medicament in the inspired air.

Figure 6:
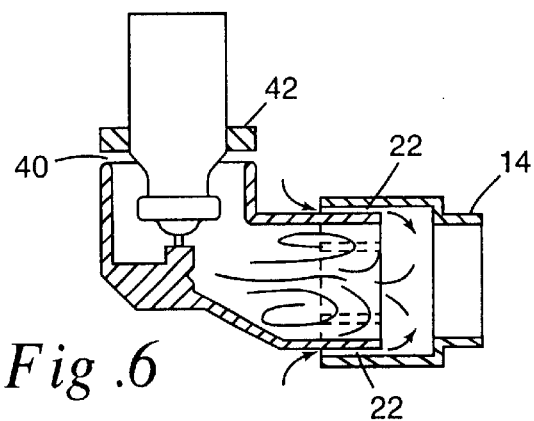
FIGS. 6 to 9 represent cross-sectional views of further inhalers in accordance with the invention.

The inhaler of FIG. 6 is based upon the inhaler of FIG. 5 and incorporates additional air inlets (22) of the type disclosed in FIG. 1.

Figure 7:
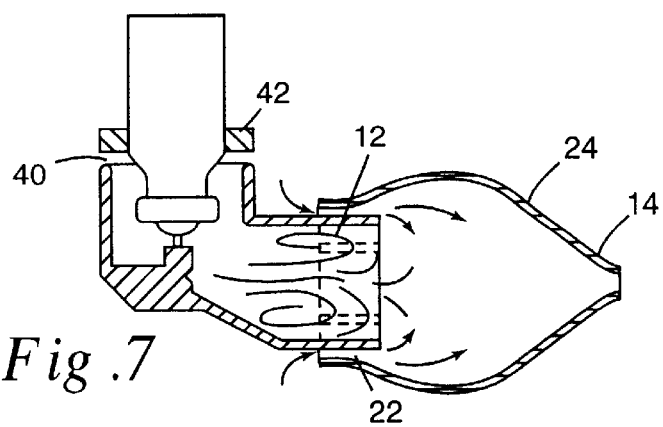

The inhaler of FIG. 7 is based upon the inhaler of FIG. 5 and incorporates a mouthpiece (14) having a bulbed configuration (24) and air inlets (22) of the type disclosed in FIG. 2.

Figure 8:
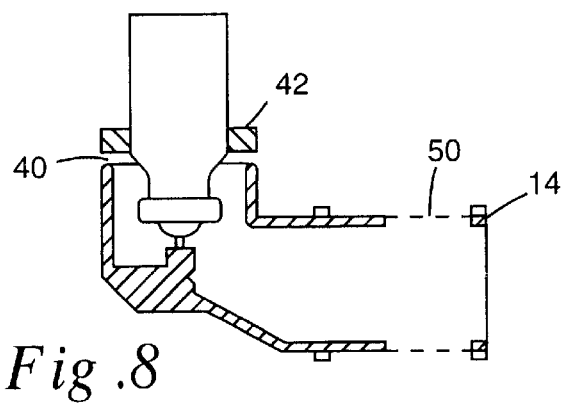

The inhaler of FIG. 8 is based upon the inhaler of FIG. 5 and incorporates air inlets in the form of a microporous membrane (50) which is positioned downstream of the turbulent zone adjacent the mouthpiece (14). The arrangement provides a multiplicity of finely divided air inlets which, upon inhalation through the mouthpiece, creates a diffuse airflow which keeps the emitted stream away from the wall of the mouthpiece.

The porous membrane material (50) must not significantly impede the patient's ability to inhale through the device. A suitable material is Whatmann No. 4 filter paper; but other materials may be used, such as those used in cylindrical air filters or membrane filters, or such as those formed by sintering polymers. A preferred porous membrane material is in the form of a cylinder made by fusing together small pellets of polypropylene.

Figure 9:
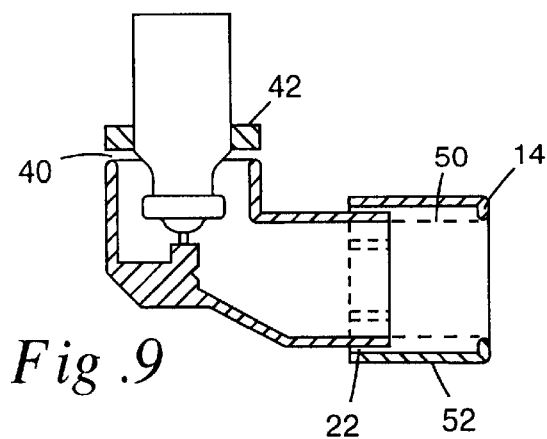

The inhaler of FIG. 9 is similar to that of FIG. 8 and additionally comprises a shield (52) to protect the microporous membrane (50) from contamination. The shield is constructed to provide air inlets (22) to direct air towards the microporous membrane (50).

Figure 10A:
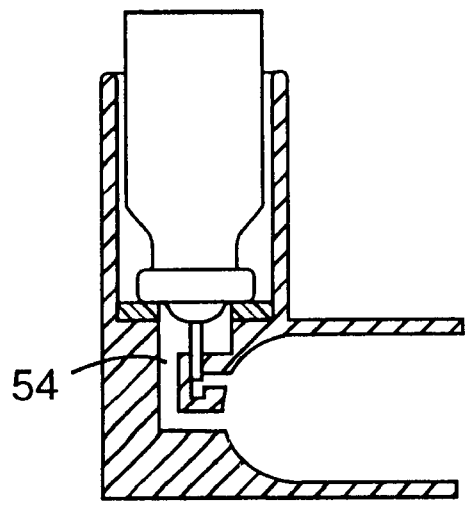
FIGS. 10(a) and (b) represent cross-sectional views of a further inhaler in accordance with the invention in its firing and rest positions respectively.
Figure 10B:
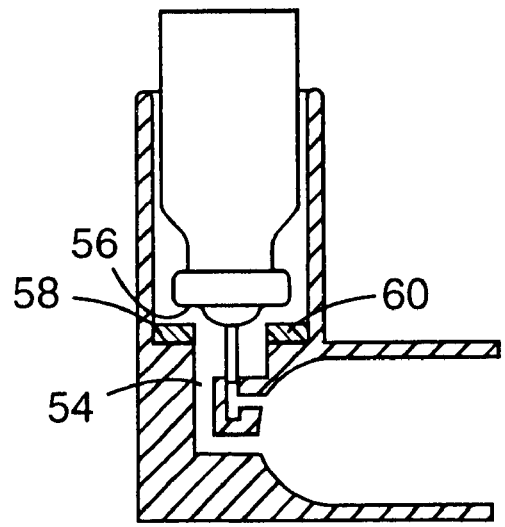

The inhaler of FIG. 10 is similar to that of FIG. 5, except that the air inlet ports (54) are closed between the flat surface of the valve ferrule (56) and a parallel ledge (58) within the actuator, by means of a seal (60), when the inhaler is in its dispensing position.

Figure 11:
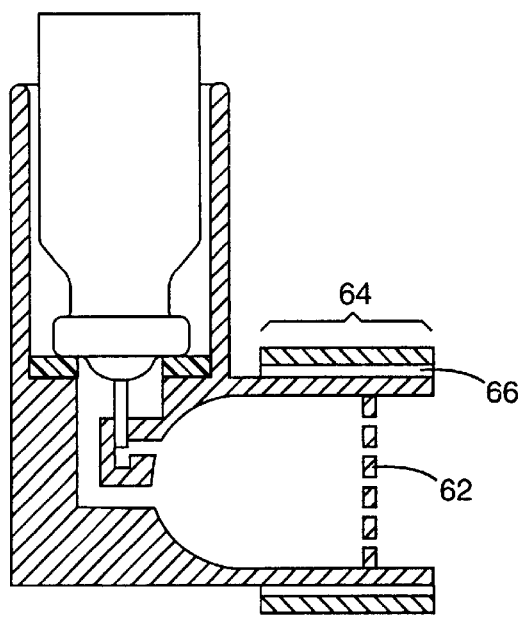
FIG. 11 represents a cross-sectional view of a further inhaler in accordance with the invention in its firing position, FIGS. 11(a) to 11(c) illustrating alternative baffles for the mouthpiece thereof and FIGS. 12a and b represent a perspective view and cross-sectional view of a nasal inhaler in accordance with the invention.

FIG. 11 shows an embodiment like that in FIG. 10, with a baffle (62) inserted. The baffle can form part of a mouthpiece component (14), like those in FIGS. 6 to 9. Alternatively, it can form part of a mouthpiece (64) which provides a sheath of air that emerges at the extreme downstream end of the inhaler. The skilled person will also appreciate that the mouthpiece (64) can substitute for mouthpiece (14) in FIGS. 6 to 9. The baffle is in the form of a thin disc defining a plurality of circular passages (65) therethrough. Preferably, there are a large number of circular passages and their accumulated area makes up a substantial proportion of the disc area as illustrated in FIG. 11a. The mouthpiece (64) has a plurality of passages (66) parallel to its axis and disposed through its circumference.

FIGS. 11b depicts a component with an alternative baffle which consists of a thin disc with a single circular hole (68).

FIG. 11c depicts another component in which the baffle consists of a disc with two kidney-shaped holes (69).

Figure 12A:
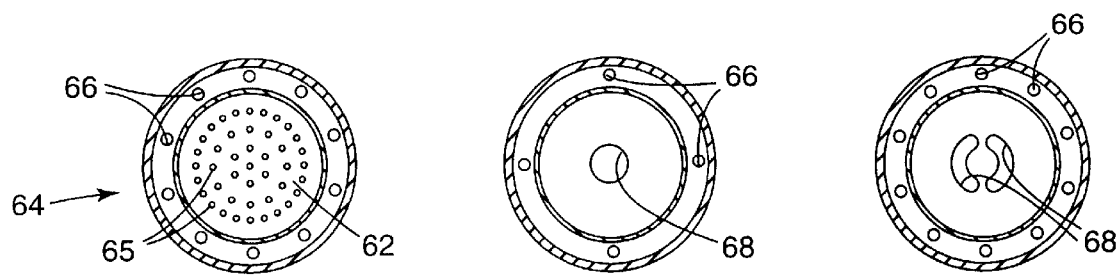
Figure 12A:
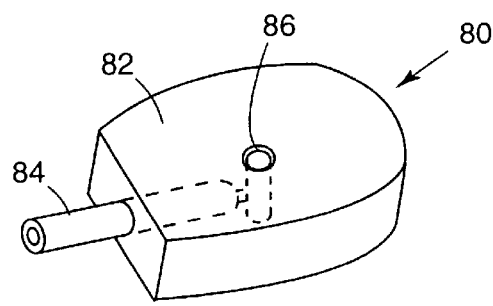
Figure 12B:
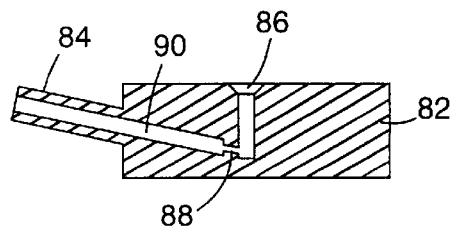

FIGS. 12a and 12b illustrate an inhaler for nasal administration of medicament. The inhaler (80) comprises a body (82) and a nosepiece (84) which is dimensioned so that it may be inserted in a nostril without being an airtight fit. The body (82) has an aperture (86) to receive the valve stem (not shown) of the pressurised aerosol, an orifice (88) communicating with a chamber (90) leading to the nosepiece (84). The valve stem forms a gas-tight seal within the orifice (88).

In use the nosepiece is inserted in a nostril and the patient inhales while actuating the valve of the pressurised aerosol container. Inhalation does not cause airflow through the inhaler (80) but an airflow is established around the outside of the nosepiece and medicament exiting the nosepiece is entrained in the airflow and delivered to the respiratory system of the patient.

The inhalers of the invention which are intended for pulmonary delivery reduce the oropharyngeal deposition. Preferred inhalers of the present invention are capable of providing improvements both in terms of oropharyngeal and lung deposition. For example, the inhaler of FIG. 8 produced a greater lung deposition and smaller oropharyngeal deposition than a metered dose inhaler fitted with a standard actuator available under the trade designation M3756 from 3M. The inhalers were compared by sealing against a cast of an upper airway and firing into air drawn through at 30 liters per minute (D. J. Velasquez and B. Gabrio 1998 J. Aerosol Med. 11 (Suppl. 1): S23–S28). The aerosol which passed through the airway was collected on a HEPA filter. Both inhalers contained beclomethasone dipropionate formulated as a radiolabelled solution. In the Table below the amount assayed by radioscintigraphy in the cast is designated 'oropharyngeal' and the amount in the filter is designated 'lung'. The inhaler produced a drug particle size equivalent to that produced by the standard inhaler with a mass median diameter of 1.4 micrometers.

|  | Standard MDI | Slow spray device |
| --- | --- | --- |
| % oropharyngeal | 35.3 | 10.0 |
| % lung | 44.2 | 54.2 |

Another advantage of inhalers of the invention is that the consequences of poor co-ordination of inhalation with actuation of the inhaler are improved compared with a standard inhaler. Disco-ordination tests were conducted on a standard press and breathe metered dose inhaler and a similar inhaler which had been modified in accordance with the invention to operate in principle as that disclosed in FIG. 1. The inhalers were tested using the equipment described above. A delay of 1 second between actuation and start of inhalation resulted in the following change in percentage regional deposition.

Change in percentage regional deposition

|  | Percent Change in Deposition | | |
| --- | --- | --- | --- |
|  | Device | Orophrarynx | Lung |
| Invention | +15 | −3 | −12 |
| Standard MDI | +41 | +8 | −49 |

What is claimed is:

1. An inhaler for medicament comprising an aerosol canister containing a pressurised medicament formulation equipped with a metered dose dispensing valve having a valve stem movable between non-dispensing and dispensing positions, and an actuator comprising a housing containing the aerosol canister and defining a chamber having a plurality of air inlets and a patient port in the form of a mouthpiece or nasal adapter through which inhalation by a patient generates an air flow, and a nozzle block adapted to receive the valve stem of the dispensing valve, the nozzle block comprising a passage in communication with the valve stem and terminating in an orifice for directing medicament from the valve stem into the chamber, wherein the actuator is constructed and arranged so as to inhibit airflow in the vicinity of the orifice of the nozzle block when the valve stem is in its dispensing position, and wherein the airflow due to patient inhalation is not prevented or inhibited in the vicinity of the orifice at all times, and wherein one of the air inlets is formed between the canister and housing when the valve is in its non-dispensing position and said one inlet is sealed when the valve is in its dispensing position.

2. An inhaler as claimed in claim 1 wherein the distance from the orifice to patient port is from 1 to 15 cm, and the mouthpiece diameter between 1 to 4 cm.

3. An inhaler as claimed in claim 1 wherein the plurality of air inlets comprise a multiplicity of numerous, small air channels which serve to provide a large surface area for air to enter the mouthpiece.

4. An inhaler as claimed in claim 3 wherein the air channels are in the form of a microporous membrane.

5. An inhaler as claimed in claim 1, comprising a baffle in the form of a thin disk defining a plurality of circular passages therethrough, configured to reduce direct contact between the medicament and the patient other than by inhalation.

* * * * *